United States Patent [19]

Ren

[11] Patent Number: 5,571,154
[45] Date of Patent: Nov. 5, 1996

[54] MICROWAVE DEEP-DIATHERMY APPARATUS

[75] Inventor: Changxue Ren, Hunan, China

[73] Assignee: Hunan University, China

[21] Appl. No.: 459,727

[22] Filed: Jun. 2, 1995

Related U.S. Application Data

[63] Continuation of Ser. No. 89,029, Jul. 19, 1993, abandoned.

[51] Int. Cl.$^6$ ..................................................... A61N 5/02
[52] U.S. Cl. ............................ 607/102; 607/156; 219/690; 219/711
[58] Field of Search .............................. 607/96, 98, 99, 607/100–102, 113, 154, 156; 219/690, 710–713

[56] References Cited

U.S. PATENT DOCUMENTS

| | | | |
|---|---|---|---|
| 4,640,280 | 2/1987 | Sterzer | 607/154 |
| 5,148,818 | 9/1992 | Kikuchi et al. | 607/101 |

FOREIGN PATENT DOCUMENTS

| | | | |
|---|---|---|---|
| 1041698 | 5/1990 | China . | |
| 0167670 | 1/1986 | European Pat. Off. . | |
| 894421 | 10/1953 | Germany | 607/100 |
| 2417263 | 10/1975 | Germany | 607/154 |
| 2508494 | 9/1976 | Germany | 607/154 |
| 862646 | 3/1961 | United Kingdom | 607/154 |

*Primary Examiner*—Lee S. Cohen
*Attorney, Agent, or Firm*—Ladas & Parry

[57] ABSTRACT

A non-contact type of deep-diathermy apparatus comprises a microwave source (1), a microwave radiator (2), a microwave focusing device (3), a temperature-measuring device (4) and a computer based control and display device (5). An output port of the microwave radiator (2) is spaced apart from a surface of a diathermized position of a medium to be diathermized by a predetermined distance. The microwave focusing device (3) is placed in front of the output port of the radiator (2) and attached to the output port of the radiator (2) for focusing the microwave from the radiator (2) on a point within the predetermined distance. This apparatus can be used to kill cancer cells or reduce their vitality in deep parts of the medium and will not cause the surface of the medium to be burnt.

10 Claims, 3 Drawing Sheets

MICROWAVE DEEP-DIATHERMY APPARATUS

CROSS-REFERENCE

This is a continuation application of U.S. Ser. No. 08/089,029, filed on Jul. 19, 1993 and now abandoned.

TECHNICAL FIELD

The present invention relates generally to microwave diathermies, more particularly to a non-contact type of microwave deep-diathermy apparatus for microwave-diathermizing both shallow parts and deep parts of lossy mediums or conducting mediums.

BACKGROUND OF THE INVENTION

Microwave diathermy has been widely used in many fields such as in the metallurgical industry, food production, medical treatment, etc. Recently, in the medical field various microwave diathermy apparatus for treating diseases, in particular, cancers, have been developed to eliminate side effects caused by radioactive and chemical therapies, and to make these therapies more effective. Microwave diathermy can be used to make polar molecules in active tissues rotate at high speeds in the microwave electromagnetic field, resulting in the generation of heat which causes the temperature of the lossy medium in the electromagnetic field to rise considerably. At such temperatures, cancer cells in a diathermical region can be killed or their vitality reduced.

An example of a microwave diathermy apparatus is the BSD-400 mobile hyperthermia system manufactured by BSD Medical Corporation of the United States of America, which a sticking-contact type of microwave diathermy apparatus comprising a microwave source with a maximum output power of 400 watts and an output frequency of 915 MHz; a circular microwave radiator with an output port used to stick on the body surface of a cancer patient for microwave-diathermizing deeply over the position of the cancer into the body of the cancer patient; an optical fiber temperature-measuring system for measuring the temperature at the position of diathermizing on the patient; and a computer based control and display system for displaying a temperature value measured by the optical fiber temperature-measuring system and for controlling and regulating the output power of the microwave source and consequently regulating the temperature at the microwave-diathermizing position to obtain the optimum therapeutic benefit in response to the temperature signal from the optical fiber temperature-measuring system. The microwave output power from the sticking-contact type of microwave-diathermy apparatus attenuates hyperbolically, as the depth of diathermy of the medium increases. In other words, the microwave power density at the output port sharply attenuates and the characteristic curve of power density-to-distance is very steep. Therefore, at the diathermized position, the temperature of the patient's body surface is higher than that under the surface, and this may easily cause the patent's skin to burn. Such a diathermy apparatus has an effective diathermic depth of 3-4 cm only, which is curative in respect of shallow tumors only, but not curative in respect of deep tumors.

In order to overcome the defects of this prior art apparatus and to increase diathermical depth, some other methods and apparatus have been developed, for example: RF-8 diathermy apparatus (Japan) with a frequency of 8 MHz, and BSD-2000 diathermy apparatus (USA) with a frequency range from 60 to 120 MHz, when a patient is treated by either of the above apparatus, the subcutaneous fat at the heated position can be easily overheated and the skin at the heated position must be cooled by water bags. Further more, since it is difficult to focus an RF electro-magnetic wave on a particular point, a large area of lossy medium has to be RF-heated, when patients are treated for chest cancer or upper-abdominal cancer, they may go into shock. Furthermore, the temperature at deeper parts of the body is not high enough, resulting in a poor curative effect.

An intracavitary diathermy method can also be used to diathermize a deep part of a lossy medium by inserting a small-sized microwave radiator into deep cavites such as the vagina, rectum, esophagus, or nasal cavity. However, only a small area can be diathermized using such a method and the internal surfaces of the cavity, might be burnt. This method can not be used in the treatment of such deep cancers as liver cancer, lung cancer and stomach cancer.

An inter-tissue diathermy method can be also used to directly heat a tumor by surgically implanting a microwave antenna or a RF electrode into the tumor. This method results in an uneven temprature distribution in the heated tumor and after a diathermical treatment the implanted microwave antenna or the RF electrode must be surgically removed. Therefore, when multiple treatments are needed this method can not be used because frequent operations have to be performed to implant and remove the antenna or electrode.

SUMMARY OF THE INVENTION

An object of the present invention is to overcome the shortcomings of the prior art microwave diathermy apparatus and methods by providing a non-contact type of microwave deep-diathermy apparatus which can be used in shallow diathermy and deep diathermy.

Another object of the invention is to provide an apparatus which has a deep diathermic depth, a uniform temperature distribution in the diathermized region, and which will not injure the diathermized surface.

Still another object of the present invention is to provide a non-contact type of microwave deep-diathermy apparatus, wherein the output port of a microwave radiator does not have to be in direct contact with a surface of a lossy medium to be diathermized, but may be separate from the surface by a predetermined distance, for example 20 cm to 70 cm. Since a microwave focussing means is provided in front of the output port of the microwave radiator for focussing the microwave beams radiated from the output port within a predetermined short distance, for example 30 cm to 80 cm, the focussed microwave energy can be concentrated on a diathermical region having a predetermined depth of, for example, 10 cm, and has little effect on the area around the diathermized region.

A further object of the present invention is to provide a non-contact type of microwave deep-diathermy apparatus with a continuously adjustable power output of up to 1.2 KW or more and a diathermical depth of more than 10 cm (under the output power higher than 1.2 KW).

A further object of the present invention is to provide a non-contact type of microwave deep-diathermy apparatus of simple construction, which can be manufactured at low cost and operated conveniently.

According to the present invention there is provided a non-contact type of microwave deep-diathermy apparatus comprising: a microwave source with a continuously adjustable power range of 0–2 KW and an output frequency ranging from 600 MHz to 1500 MHz; a microwave radiator having an input port and an output port with its input port coupled with an output of the microwave source for receiving the microwave energy at the input from the microwave source and radiating the energy through its output port; a temperature-measuring means for measuring a surface temperature and deep tissue temperatures of a medium to be diathermized; a computer based control and display means having a plurality of I/O interfaces to couple with the temperature-measuring means and the microwave source respectively, and being responsive to a temperature signal from the temperature-measuring means for displaying a temperature value measured by the temperature-measuring means and correspondingly providing a control signal for the microwave source to control and adjust the output power of the microwave source and to consequently change the temperature of the diathermized portion of the medium being diathermized; wherein microwave focussing means are provided in the front of the output port of the microwave radiator and attached to the output port of the microwave radiator, for focussing the microwaves from the microwave radiator on a point within a predetermined short distance, for example 30 cm to 80 cm, from the output port of the radiator. The focussing means comprises a casing and a plurality of small metal balls placed within and supported by the casing and arranged in a convex lens shape with the balls being substantially evenly in a spaced dot array, characterized in that the output port of the microwave radiator does not directly contact with the surface of the medium to be diathermized, but is spaced a predetermined distance, for example 20–70 cm, from the surface of the medium, and the small metal balls are either solid bodies or hollow bodies having an external diameter of 1.5–4 cm and the distance between any two of the balls being 2–5 cm.

The present invention is based on the theory of spherical electromagnetic wave diathermy proposed by the inventor of the present invention. In accordance with this theory, the electromagnetic wave radiated by a circular radiator or a rectangular radiator approximates a spherical wave, rather than a plane wave. For a spherical wave, the microwave power density attenuates rapidly at points near the output port of the microwave radiator resulting in shallow diathermy, and at points further from the output port, the microwave power density attenuates slowly and the diathermy is deep.

According to this theory, the output port of the microwave radiator can be spaced apart from the surface of the medium to be diathermized at a predetermined distance for example 20–70 cm. Thus, a microwave focussing means can be provided in the front of the output port of the radiator. Since there is a distance between the output port of the microwave radiator and the surface of the medium, the output power of the microwave source needs to be increased. In the present invention, the maximum continuous output power should be more than 1.2 KW for the diathermical depth of more than 10 cm.

Since the microwave diathermy apparatus of the present invention has a focussing means for focussing the microwave on a point within a short distance from the output port, the shortcomings of the prior art diathermy apparatus such as shallow diathermic depth, injury to the surface of a medium and uneven temperature distribution in a diathermic region are overcome.

In medical applications, the microwave deep-diathermy apparatus of the present invention can be used to treat deep chest, abdominal or limb cancers, such as carcinoma of the esophagus, carcinoma of the stomach, lung cancer, liver cancer, intestinal cancer, carcinoma of the uterus, etc., and to treat such diseases as arthritis, prostatitis, lumbar muscle strain, etc. Clinical tests have been successfully conducted using the microwave deep-diathermy apparatus of the present invention to treat many critically ill patients suffering from advanced cancers. The present invention has demonstrated its usefulness in treating cancer patients.

Further objects, advantages and other features of the present invention will become more apparent upon reading of the following non-restrictive description of the preferred embodiment thereof, given for the purpose of exemplification only, with reference to the accompanying drawings.

DETAILED DESCRIPTION OF THE PREFERRED EMBODIMENT

Figure 1:
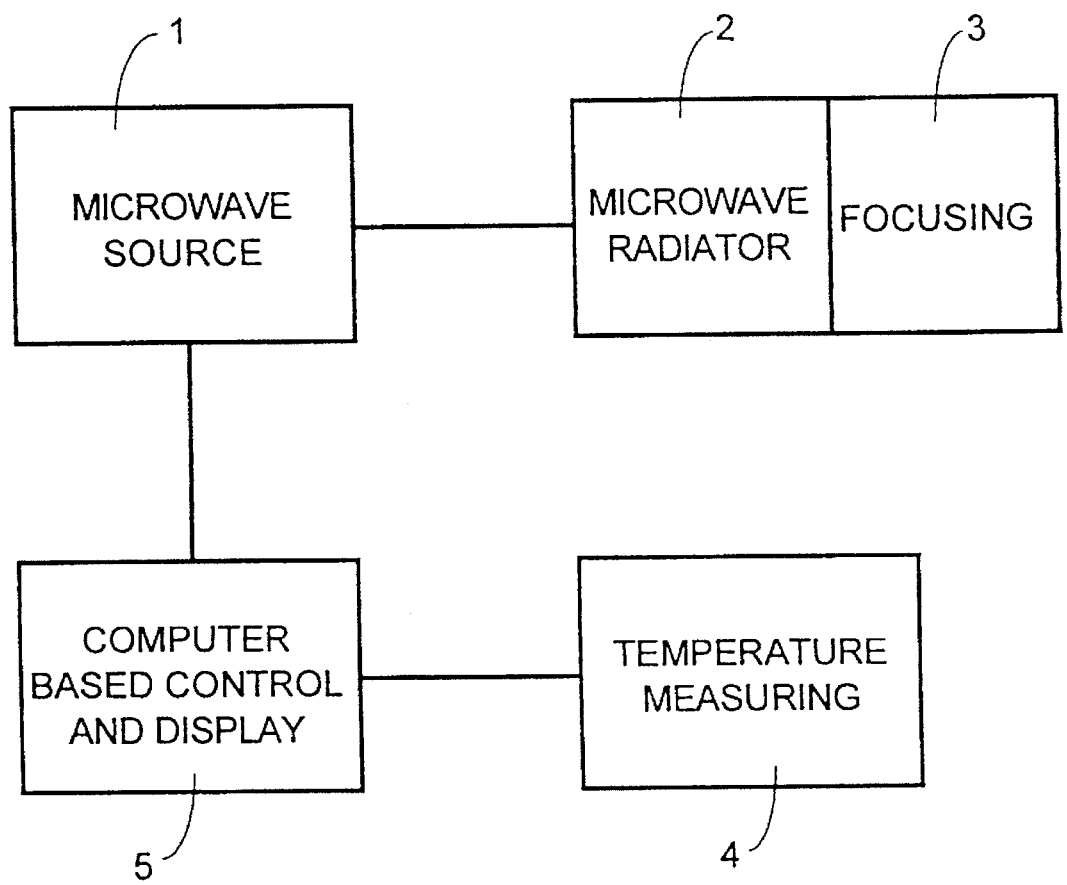
FIG. 1 is a block diagram illustrating the microwave deep-diathermy apparatus of the present invention.

FIG. 1, is a block diagram of the microwave deep-diathermy apparatus of the present invention. As shown in FIG. 1, the microwave deep-diathermy apparatus comprises: a microwave source 1, a microwave radiator 2, a microwave focussing means 3, a temperature-measuring means 4 and a computer based control and display means 5.

The microwave source 1 is for example a conventional microwave source, which generates microwaves having a continuously adjustable output power range of 0–2 KW and an output frequency range of 600–1500 MHz. In the embodiment described here, the frequency is 915 MHz.

The microwave radiator 2 is for example a conventional circular microwave radiator with a caliber of 15 cm, having an input port coupled with the output of the microwave source 1 by a coaxial cable, and an output port not directly contacting with the surface of a medium to be diathermized and being spaced apart from the surface by a predetermined distance for example 20–70 cm. 70 cm.

The microwave focussing means 3 is placed in the front of the Output port of the microwave radiator 2 and attached to the output port of the microwave radiator 2, for focussing the microwaves radiated by the microwave radiator 2 on a point within a predetermined distance from the output port of the microwave radiator 2. The particular structure of the focussing means will be described below in detail.

Figure 4A:
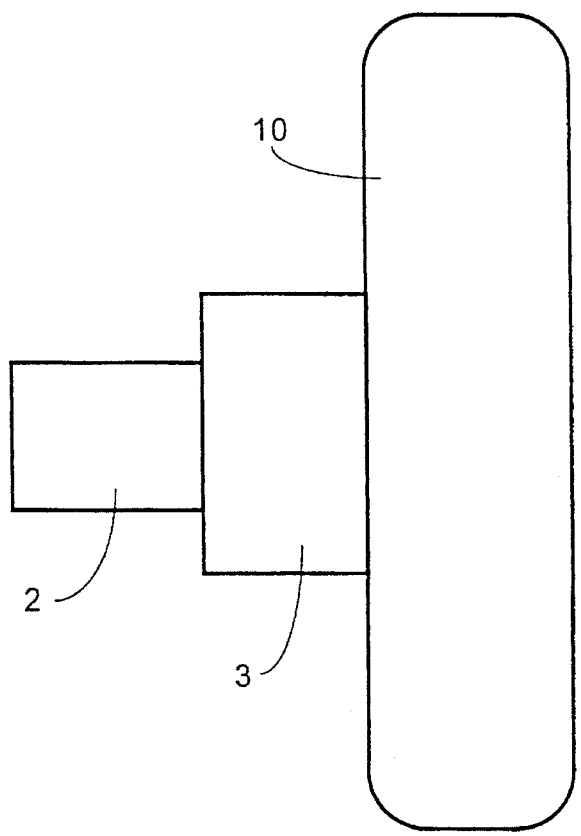
FIGS. 4A and 4B illustrate the position of the microwave radiator and the focusing means with respect to the medium to be diathermized.
Figure 4B:
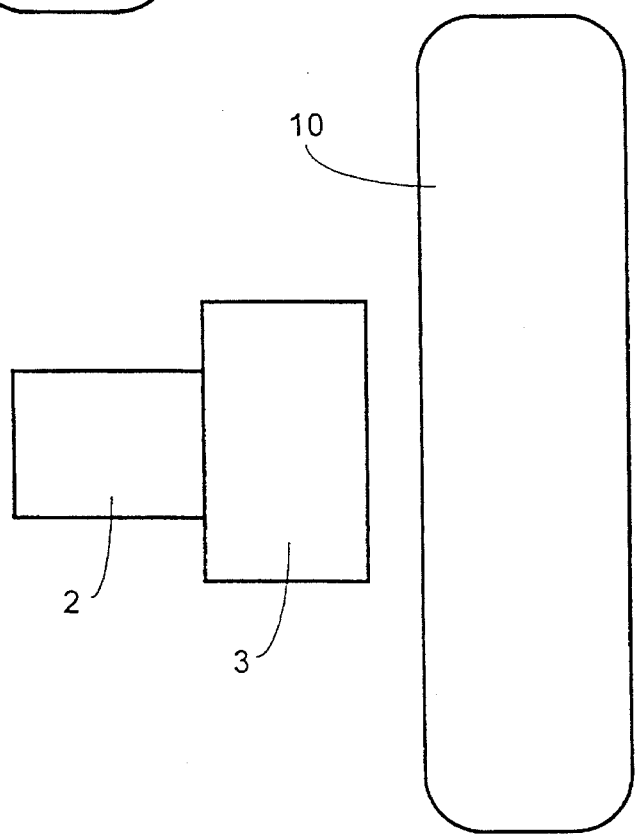

FIG. 4A shows an extreme situation that the focusing means 3 may be in contact with the medium 10. However, in normal operation, the focusing means 3 does not contact with the medium 10 as shown in FIG. 4B. In any event, the output port of the microwave radiator does not directly contact with the surface of the medium 10.

The temperature-measuring means 4 is for example a conventional optical fiber temperature-measuring device or infrared temperature-measuring device, for measuring the surface temperature and deeper temperatures at the position where the medium is being diathermized.

The computer based control and display means 5 is for example a CPU-Model 286 or 386 computer which has a plurality of I/O interfaces for interfacing with the microwave source 1 and the temperature-measuring means 4, and which displays the temperature value and provides a control signal for the microwave source 1 in response to a temperature signal from the temperature-measuring means 4. The control signal is used to control and adjust the output power of the microwave source 1 and consequently to change the temperature of the medium being diathermized.

Figure 2:
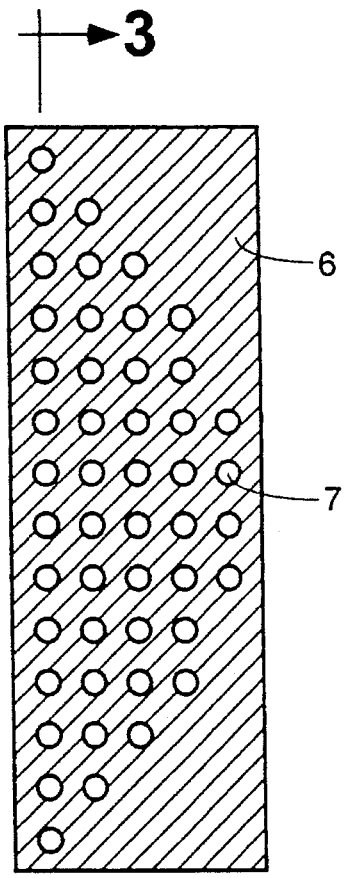
FIG. 2 is a plane view of a preferred embodiment of the focussing means in the microwave deep-diathermy apparatus of the present invention.
Figure 3:
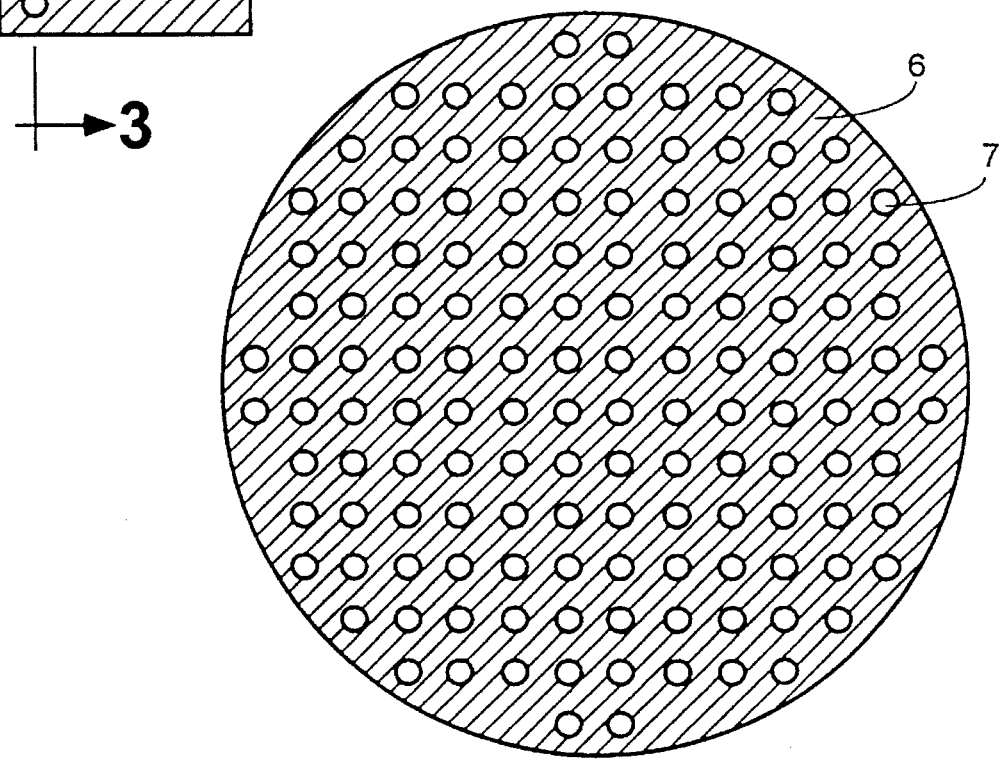
FIG. 3 is a cross-sectional view of the focussing means taken along line A—A in FIG. 2.

FIGS. 2 and 3 show plane and cross-sectional views of the microwave focussing means 3 in the microwave deep-diathermy apparatus of the present invention. As shown in FIGS. 2 and 3, the microwave focussing means 3 comprises a casing 6 and a plurality of small metal balls 7. The casing 6, for example, is made from foam plastics. The small metal balls 7 are placed in and are supported by the casing 6 and arranged as a convex lens shape with the balls being spaced substantially evenly in a spaced dot array having a focal distance of 30–80 cm and perferably 40–50 cm. The small metal bails are either solid bodies or hollow bodies, having an outside diameter of 1.5–4 cm and the distance between two balls is 2–5 cm. A test of microwave diathermy has been conducted on a living pig of 80 Kg using the microwave deep-diathermy apparatus of the present invention. The diathermized part was the abdomen of the living pig. The test conditions was as follows:

Microwave frequency: 915 MHz

Output power of Microwave Source: 2 KW

Distance between the output port of the microwave radiator and the abdomen of the pig: 30 cm.

The test results are as follows:

| Diathermical depth (cm) | temperature (°C.) |
| --- | --- |
| 0 | 38.3 |
| 1 | 41.6 |
| 2 | 42.3 |
| 3 | 42.6 |
| 4 | 42.7 |
| 5 | 42.6 |
| 6 | 42.5 |
| 7 | 42.3 |
| 8 | 42.1 |
| 9 | 42.0 |
| 10 | 41.9 |
| 11 | 41.7 |
| 12 | 41.6 |

The test results indicate that the temperature differs slightly and is generally uniform within the diathermical depth range of 0–12 cm. At these temperatures, cancer cells can be killed or their vitality can be reduced and the surface of the medium can not be burst because the temperature not high enough.

When the microwave deep-diathermy apparatus of the present invention is used to treat a cancer patient, the patient will only feel hot in the deep diathermized part of the body, and no uncomfortable sensations or side effects will be experienced. The microwave deep-diathermy apparatus is safe, reliable, easy to operate and has notable curative effects.

Although the present invention has been explained above by way of a preferred embodiment thereof, it should be pointed out that any modifications to these preferred embodiments within the scope of the appended claims is not deemed to alter or change the nature of the scope of the present invention.

I claim:

1. A non-contact type of microwave deep-diathermy apparatus adapted for diathermizing a medium including a surface, comprising:

a microwave source including an output for providing microwaves, said microwave source having a continuously adjustable output power with a maximum output power of more than 1.2 kw and an output frequency range of 600–1500 MHz;

a microwave radiator having an input port and an output port with the input port coupled with the output of said microwave source for receiving said microwaves from said microwave source and radiating them through the output port thereof, said microwave radiator adapted for radiation toward said medium and being non-contact with the medium, wherein a distance between the surface of the medium and said output port of the microwave radiator is 20–70 cm;

microwave focusing means provided in front of said output port of said microwave radiator and attached thereto for focusing said radiating microwaves on a point positioned in the medium, the focusing means having a focal distance of 30–80 cm;

temperature-measuring means for measuring a surface temperature and deep tissue temperatures of said medium; and computer based control and display means coupled with said temperature-measuring means and said microwave source respectively, and responsive to a temperature signal from said temperature-measuring means for displaying a temperature value measured by said temperature-measuring means and providing a corresponding control signal for said microwave source to control and adjust the output power of said microwave source and consequently change the temperature of a diathermized position in the medium to be diathermized.

2. The apparatus of claim 1, wherein said microwave focusing means comprises a casing and a plurality of small metal balls placed in and supported by said casing and arranged as a convex lens shape with the balls being arranged in a spaced dot array.

3. The apparatus of claim 2, wherein each of said small metal balls is of a solid body with a diameter of 1.5–4 cm and a distance between any two of the balls is 2–5 cm.

4. The apparatus of claim 2, wherein each of said small metal balls is of a hollow body with a diameter of 1.5–4 cm and a distance between any two of the balls is 2–5 cm.

5. The apparatus of claim 1, wherein the output frequency of said microwave source is 915 MHz, and the maximum output power of said microwave source is 2 kw.

6. A non-contact type of microwave deep-diathermy apparatus adapted for diathermizing a medium including a surface, comprising:

a microwave source including an output for providing microwaves, said microwave source having a continuously adjustable output power with a maximum output power of more than 1.2 kw and an output frequency range of 600–1500 MHz;

a microwave radiator having an input port and an output port with the input port coupled with the output of said microwave source for receiving said microwaves from said microwave source and radiating them through the output port thereof, said microwave radiator adapted for radiation toward said medium and being non-contact with the medium, wherein a distance between the surface of the medium and said output port of the microwave radiator is 20–70 cm;

microwave focusing means provided in front of said output port of said microwave radiator and attached thereto for focusing said radiating microwave on a point positioned in the medium, wherein said microwave focusing means comprises a casing and a plurality of small metal balls placed in and supported by said casing and arranged as a convex lens shape with the balls being arranged in a spaced dot array;

temperature-measuring means for measuring a surface temperature and deep tissue temperatures of said medium; and computer based control and display means coupled with said temperature-measuring means and said microwave source respectively, and responsive to a temperature signal from said temperature-measuring means for displaying a temperature value measured by said temperature-measuring means and providing a corresponding control signal for said microwave source to control and adjust the output power of said microwave source and consequently change the temperature of a diathermized position in the medium to be diathermized.

7. The apparatus of claim 6, wherein the focusing means has a focal distance of 30–80 cm.

8. The apparatus of claim 6, wherein each of said small metal balls is of a solid body with a diameter of 1.5–4 cm and a distance between any two of the balls is 2–5 cm.

9. The apparatus of claim 6, wherein each of said small metal balls is of a hollow body with a diameter of 1.5–4 cm and a distance between any two of the balls is 2–5 cm.

10. The apparatus of claim 6, wherein the output frequency of said microwave source is 915 MHz, and the maximum output power of said microwave source is 2 kw.

* * * * *

UNITED STATES PATENT AND TRADEMARK OFFICE
CERTIFICATE OF CORRECTION

PATENT NO. : 5,571,154

DATED : Nov. 5, 1996

INVENTOR(S) : Changxue Ren

It is certified that error appears in the above-identified patent and that said Letters Patent is hereby corrected as shown below:

On the Title page, item [63] Related U.S. Application Data; "Jul. 19, 1993" should read --Jul. 9,1993.

Signed and Sealed this

Eleventh Day of March, 1997

*Attest:*

BRUCE LEHMAN

*Attesting Officer*     *Commissioner of Patents and Trademarks*